(12) United States Patent
Konesky

(10) Patent No.: US 8,377,388 B2
(45) Date of Patent: Feb. 19, 2013

(54) COLD PLASMA DECONTAMINATION DEVICE

(75) Inventor: Gregory Konesky, Hampton Bays, NY (US)

(73) Assignee: Bovie Medical Corporation, Clearwater, FL (US)

( * ) Notice: Subject to any disclaimer, the term of this patent is extended or adjusted under 35 U.S.C. 154(b) by 488 days.

(21) Appl. No.: 12/012,446

(22) Filed: Feb. 2, 2008

(65) Prior Publication Data

US 2010/0284867 A1 Nov. 11, 2010

(51) Int. Cl.
*A61L 2/00* (2006.01)
(52) U.S. Cl. .......................................... 422/292; 422/28
(58) Field of Classification Search ............... 422/28, 422/292, 26
See application file for complete search history.

(56) References Cited

U.S. PATENT DOCUMENTS

| 4,897,285 | A | 1/1990 | Wilhelm |
| 6,170,668 | B1* | 1/2001 | Babko-Malyi ............. 209/127.1 |
| 6,492,951 | B1 | 12/2002 | Harris et al. |
| 6,627,163 | B1* | 9/2003 | Awakowicz et al. ...... 422/186.23 |
| 6,764,658 | B2* | 7/2004 | Denes et al. ............. 422/186.04 |
| 7,070,144 | B1 | 7/2006 | DiCocco et al. |
| 7,275,013 | B1 | 9/2007 | Matlis et al. |
| 7,615,933 | B2* | 11/2009 | Hooke et al. .............. 315/209 R |
| 2004/0116918 | A1 | 6/2004 | Konesky |
| 2005/0118350 | A1* | 6/2005 | Koulik et al. ................. 427/535 |
| 2006/0005545 | A1 | 1/2006 | Samimy et al. |
| 2007/0089795 | A1 | 4/2007 | Jacob |

FOREIGN PATENT DOCUMENTS

WO WO2006100030 * 9/2006

* cited by examiner

*Primary Examiner* — Kevin Joyner
(74) *Attorney, Agent, or Firm* — Gerald E. Hespos; Michael J. Porco; Matthew T. Hespos

(57) ABSTRACT

A cold plasma device for large area decontamination that can function as a scrub brush to sterilize surfaces and areas that are otherwise difficult, time-consuming and/or may cause exposure hazards under convention sterilization methods.

20 Claims, 1 Drawing Sheet

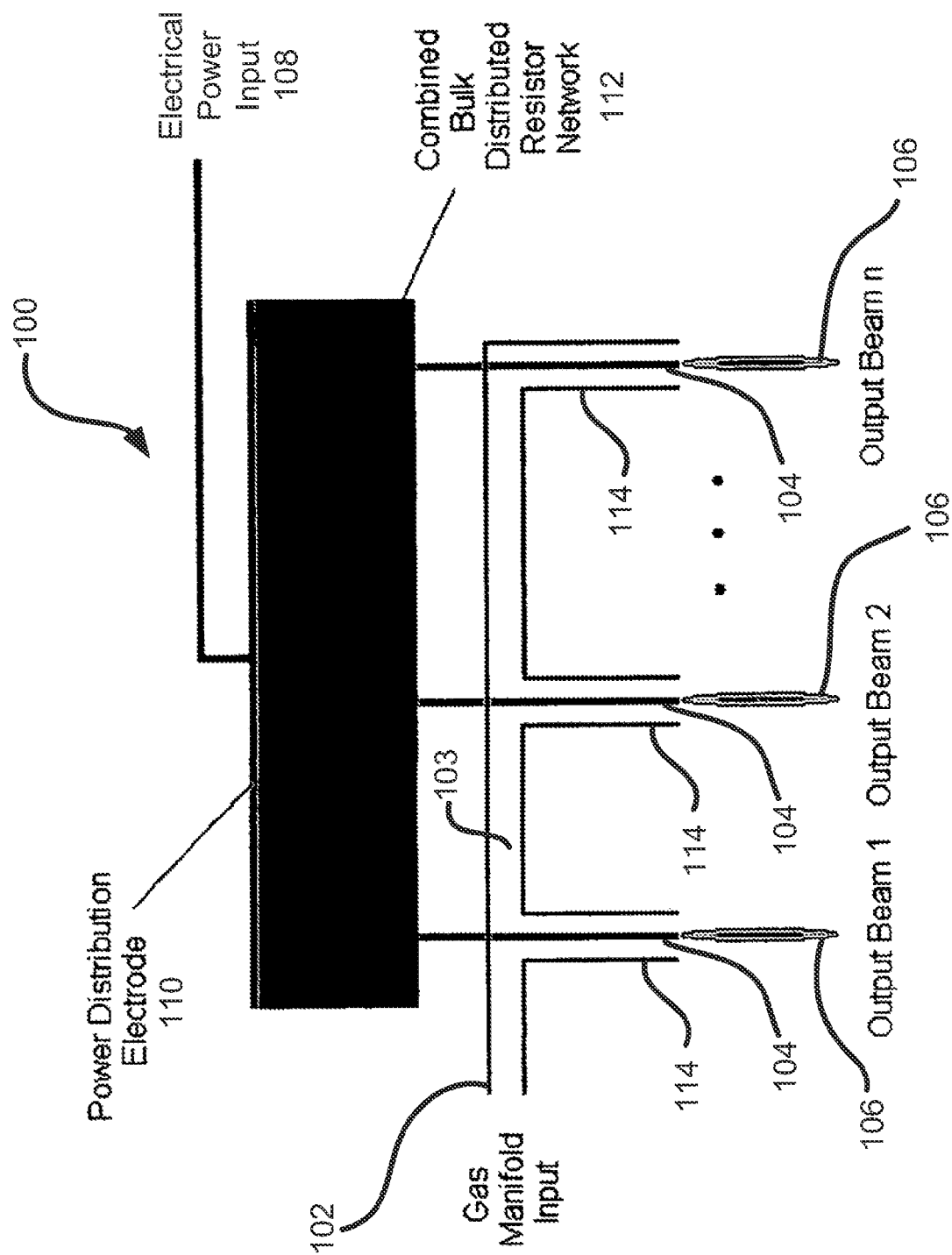

COLD PLASMA DECONTAMINATION DEVICE

FIELD OF THE INVENTION

A large-area cold plasma decontamination device for decontamination of nuclear, biological, medical and chemical incidents in military, industrial and civilian situations.

BACKGROUND

Atmospheric discharge cold plasma technology has been employed by the medical community for several years. Examples of high power uses include tissue ablation, suture sealing and sterilization of a tissue area. Low power uses may include dermatologic, hemostasis and other health-field related applications.

The term "cold plasma" is used to indicate that only a small fraction of the inert carrier gas is ionized, although this fraction can be adjusted to suit the particular use or application. Typically, the ionized portion of the carrier gas can range between approximately $10^{-6}$ (a very weak plasma beam) to approximately $10^{-3}$ (a strong beam). A plasma can be formed where a gas is exposed to a specific amount of energy, and that energy exposure separates the gas component molecules into a collection of ions, electrons, charge-neutral gas molecules, and other species in varying degrees of excitation. Effectiveness has been demonstrated in rapid sterilization, decontamination and industrial processing. Unlike semiconductor industry applications, the cold plasma technology does not require a vacuum chamber. The plasma discharge is conducted in the open air.

The mean electron energy (or temperature) of a cold plasma is considerably higher than that of the bulk-gas molecules. Energy is primarily added to the electrons rather than the ions and background gas molecules, and the electrons can attain energies of approximately $10^{-1}$ eV or higher, while background gas remains at ambient temperature. A significant energy savings can be realized since electrons are preferentially excited and larger ions are left in a lower energy state in a cold plasma.

A plasma may also be formed when a modulated electric field is applied to a pair of electrodes and exposed to the gas. The plasma formation can cause oxygen molecules of the air passing near the electrodes to break down into component molecules, including reactive oxygen species ("ROS"). Organic substrates, such as bacteria, viruses, microbes and mold spores can be exposed to ROS, and then destroyed or rendered harmless rapidly. The same reaction can convert much or all of the ROS back into oxygen.

Cold plasmas can provide rapid decontamination of clothing, equipment or gear, and sterilization of medical equipment or food. However, while present methods of decontamination and sterilization may require long periods of time, even hours or days and generate damaging heat in the process; a cold plasma of the present disclosure can often sanitize an area or object very briefly, in seconds or minutes.

It would be advantageous in a number a fields to provide a cold plasma that can decontaminate or sterile large areas rapidly.

SUMMARY OF THE INVENTION

This disclosure relates to a decontamination Device having, at least, a gas source, where the gas is typically an inert gas, a gas manifold, at least one resistor network, which may be formed of various types of resistors, and a power source. The Device forms a plasma that may be employed to decontaminate large areas rapidly and efficiently in a variety applications.

FIGURES

FIG. 1 is a cross-sectional view of the general formation of the bulk distributed resistor.

DETAILED DISCLOSURE

The disclosed atmospheric discharge cold plasma device (the "Device") is a large-area mechanism to provide decontamination, sterilization and general "clean-up" with, inter alia, nuclear fallout or waste, biologicals, chemicals, and industrial waste. The Device may be employed in any setting, including in urban outdoor areas, in medical facilities, military facilities, airplane hangers, storage facilities, inside tanks and other holding facilities, and the like. The Device may be operated remotely, preset for operation, or manually operated. It may also be disposable or reusable. The Device provides great advantages over the cold plasma prior art, which is generally directed to medical uses, because very large areas may be decontaminated or sterilized rapidly, and no prior preparation of the area is required in any way. Electrosurgical uses of plasma are disclosed in, inter alia, U.S. Application 2004/0116918, which is incorporated herein in its entirety.

The Device's plasma beam is emitted via the applicator portion of the Device and can have multiple modes of action to achieve the desired effect. These modes include ion bombardment, electron bombardment, thermal effects, ultra-violet emissions, and the local generation of ozone. Via any of these modes, and combinations thereof, the flowing inert carrier gas can help carry away debris, and expose a clean, fresh surface. The ratio of electrical energy input to carrier gas flow rate can be adjusted over a wide range, to allow the overall effect to be varied over a wide range.

The device has a scalable approach to producing a large area plasma applicator, which can range from approximately one millimeter diameter pin-point beam to a much larger area beam array, which may be approximately a square meter area or more. A large plasma beam area can be employed as a plasma scrub brush for use in a variety of situations for decontamination and/or sterilization. Devices can be built in a manner that allows flexibility and can adjust to contoured surfaces. Such flexibility may be employed in an even wider number of circumstances including holding tanks, reactors, and the like.

One of the primary benefits of the Device, and atmospheric discharge cold plasma technology, is the combined impact of multiple modes of action that provide an antimicrobial action against a wide spectrum of organisms and spores, including bacteria, viruses, microbes, fungi, and the like. This same effect would allow for decontamination of a wide spectrum of biological agents typically deployed in biological weapons of mass destruction, and yet cause little or no collateral damage to the substrate during decontamination. The Device can be formed to permit safe and relatively rapid decontamination of large affected areas as compared to more typical or traditional clean-up methods. In addition, the Device does not use hazardous chemicals or generate hazardous waste streams, unlike previously known devices and clean-up methods.

The Device may also be employed against chemicals using the same modes of plasma action by breaking down chemical bonds of chemical weapons agents, by reducing chemicals to simple compounds such as water, carbon dioxide, and the like. The Device as a plasma scrub bush would be particularly effective to decontaminate porous substrates and surfaces which are highly problematic in such situations. The Device can decontaminate the porous surfaces of these substrates because the individual plasma beams can travel to the substrate surface despite uneven surface levels. Again, the Device has little or no deleterious effect(s) on the substrate itself.

The Device may also be used to remove, isolate or destroy radioisotope compounds, particularly those associated with weapons. Currently, no technology exists in the prior art to reduce the specific activity of radioisotopes, which can be deployed in a weapon, or so called "dirty bomb". The goal of removing and isolating radioisotopes from the affected area can be accomplished by applying the cold plasma technology in a practical large area applicator such as the plasma scrub brush. The Device frees the isotopes from the contaminated surface for subsequent removal. For example, a radioactive compound can be broken down into its constituent components, including water. The isotope can then be removed from the substrate with the Device and disposed of readily with the other components.

Plasma "preprocessing" is employed in various industries to remove contaminants from surfaces. At higher powers, the plasma preprocessing can also roughen surfaces on a micro scale and in the case of polymers, create dangling bonds. These processes are used to enhance subsequent surface procedures such as coatings, adhesion and the like but typically require the use of a vacuum chamber in the prior art to apply a plasma at sub-atmospheric pressures. This is particularly problematic with large or oddly shaped/non symmetrical objects or surfaces. The Device can be employed to preprocess or treat objects of any arbitrary size or shape in a safe environment. Preprocessing with the Device can also permit rapid assessment of effectiveness of any preprocessing procedure, and allow subsequent processes to proceed as may be necessary without breaking a vacuum seal, if a vacuum used. For example, preprocessing of surfaces for hip or knee implant replacements can improve bone adhesion(s). Preprocessing can also, for example, promote adhesion of non-stick materials to other substrates or assist adhesion of markings to surfaces where the necessary markings would otherwise wipe off.

The Device may be formed in any convenient physical size depending on an intended use. Medical use Devices may be small hand-held tools or larger wall-mounted tools on swing arms or tracks to be positioned as necessary during a medical procedure. Medical Devices may be formed as single-use articles or multiple use with re-sterilization. Larger Devices may be formed in the sizes of household or industrial vacuums, or in any convenient size that may fulfill a particular or general use need. The Device may use any convenient power source, which may generally be determined by the intended use at the time of manufacture. For example, a Device intended for reuse or multiple uses that might be employed, for example, in a hospital setting may run via an electrical cord. Alternatively, a Device that is manufactured for a one time use may be run on a battery, or, perhaps, a solar charge battery for larger areas.

The Device 100 can include a gas storage tank, or holding location, and typically the gas would be a noble or inert gas, such as helium or argon. The gas storage tank can be operatively connected to a conduit 102 to provide a source of gas to be fed into the Device. The conduit 102, in turn, leads to the electrodes 104. The electrodes 104, when activated, at least partially ionize the gas to create the plasma stream or streams 106. The number of plasma streams 106 will be dependent on the size of the Device 100 itself, and the size of the Device applicator which may be formed as large as approximately a square meter or more.

Power input 108 into the Device 100 can run through a power distribution electrode 110 into a bulk distributed resistor 112, as described below, or individual ballast resistors depending on the size of the applicator. A plasma beam 106 can be formed by passing the gas over a sharp conductive point, generally of an electrical flow wire, which is held at a relatively high voltage, generally greater than 1 KV, and at a relatively high frequency, generally in the range of approximately 10 KHz to approximately 10 GHz. Alternatively, a sintered metal component may be employed to provide a sharp conductor necessary to create the strong electric field gradient which helps pull electrons off the inert gas molecules and ionize them. The metal particle edges of a sintered metal component can act as sharp conductive points. Ballast resistors may be employed to prevent plasma beams from simultaneously functioning or firing, as depicted in FIG. 1. The plasma beam may exhibit negative resistance and can prevent additional beams from functioning or firing. The associated resistance values can range from approximately 1 K$\Omega$ to approximately 10 M$\Omega$.

Individual resistors, at least one resistor or a plurality of resistors, may be used in cases where the number of resistors necessary or required to function with the area of a particular applicator would not become unwieldy. However, individual resistors can be problematic where large numbers of resistors may be involved as in large area applicators. Rather than employ several hundreds or thousands of resistors for use with one applicator, a combined bulk distributed resistor can be used as a resistor network.

The bulk distributed resistor can be formed of a slow cure epoxy that can be blended with at least one conductive component to produce a desired level of equivalent resistance. Alternatively, the bulk distributed resistor may be formed of other materials, such as, for example, room-temperature vulcanizing ("RTV") rubber, silicones, polymers, and other materials and combinations that can combine with conductive components and that can be hardened or harden sufficiently for use. The conductive component can be formed of carbon nanotubes, carbon fibers, graphite powers, conductive metal particles, conductive metal oxides, conductive polymers, or a combination thereof. The conductive component may form a percentage of the resistor material in the range of approximately 0.1% or less to approximately 80% or some what higher. In another embodiment, the amount of conductive materials formed in the resistor may be in the range of approximately 25% to approximately 60%. In yet another embodiment, the amount of conductive materials formed in the resistor may be in the range of approximately 35% to approximately 45%. The epoxy is poured into an appropriate mold, depending, inter alia, on the desired size, shape and flexibility for a particular form of the Device. The epoxy may then be subjected to vacuum degassing to remove most, if not all, of any air bubbles that may have formed during the molding process.

The bulk distributed resistor can be formed in a pin grid array. A pin grid array can be inserted into the epoxy to an approximate depth of not more than half the depth of the mold and rigidly held in the desired position until the epoxy has cured. Once the epoxy has cured, the hardened epoxy is removed from the mold and the pin array, leaving individual channels for emitting a plasma beam through the applicator. The equivalent resistance of the bulk distributed resistor can have values of approximately 1 K$\Omega$ to approximately 10 M$\Omega$ between any pin and a common distribution electrode.

A common distribution electrode 110 can be attached to the epoxy surface near the power input source 108. The electrode 110 may be formed of conductive paints, an additional epoxy layer of higher conductivity, a metal plate or some combination thereof. A plurality of channels may be formed through the bulk resistor to allow electrical flow, or other type of power, to contact the gas as the gas flows through a gas manifold 103 having an input 102 that is connected, directly or indirectly, to the gas storage tank. The electrical flow can ionize the gas as the power passes into the gas manifold 103 and forms a plasma stream 106 at the point of the electrical flow wire 104. The plasma stream 106 may then flow through an emitter or output channel 114 that is operatively formed on the gas manifold 103 approximately opposite the bulk resistor 112. A myriad number of plasma beam emitters 114 may be formed. The emitters 114 can transect the Device applicator to allow the plasma beams 106 to contact a surface outside the Device 100. Decontamination of a surface in contact with the Device's plasma beam 106 then occurs rapidly, with seconds or minutes. Decontamination time frames may vary based on a number of factors, including the type of surface, the type of contamination, additional biological and/or chemical compounds present, and temperature.

Alternatively, an intermediate electronegative gas conduit may optionally be disposed in a coaxial relationship relative to the gas conduit. A second gas conduit can be used to supply an electronegative gas, or air such as oxygen and nitrogen to maintain the plasma stream. Optionally, an outer aspiration conduit may also be coupled to a negative pressure source, such as a vacuum, that can be disposed in surrounding coaxial relationship, and also recessed, relative to the electronegative gas conduit. An aspiration conduit can optionally be used to remove fluid and solid debris from the decontamination area, if desired.

Generally, oxygen and nitrogen in the atmosphere surrounding a plasma beam can tend to confine the plasma discharge to an elongated narrow beam. However, if plasma is applied to an enclosed or internal cavity, the gas flow from the plasma stream displaces any air remaining within the cavity. In order to maintain the profile of the plasma stream within a confined space, the intermediate electronegative gas conduit can be employed. This intermediate electronegative gas conduit extends beyond the inner gas conduit in order to maintain a laminar coaxial flow. Gas and air flow rates are generally equal. However, air flow rates in excess of the gas flow rate can be used to enhance flow-assisted removal of smoke and debris generated during use of the Device, if desired. Excessive flow rates of either the gas or air can induce turbulence in the plasma stream and distort the discharge jet shape.

Cross-boundary diffusion from the plasma stream into the surrounding air and air diffusion into the plasma stream can limit the effective length of the plasma stream. Inert gas can be substituted in place of additional gas flow in the intermediate electronegative gas conduit, which can significantly extend the plasma stream, if desired for a specific environment. A reduced concentration gradient of the gas can occur from an ionized jet diffusing into non-ionized gas and vice versa. This reduced concentration gradient can result in an overall plasma stream that can be approximately two and two and one-half times as long as plasma streams without a coaxial gas flow.

It will be appreciated that the disclosed Device addresses the pressing problem of decontaminating an area without further risk to life or exposure. A contaminated area can be secured and sterilized or decontaminated without direct human contact in a large number of settings that would prove unsafe or even dangerous for humans in short term or prolonged contact with the contaminants. The Device is also ideal for decontamination of interior surfaces and areas, such as holding tanks, because the Device can be formed using a flexible applicator to adapt to specific environments and uses, and avoid human exposure to high contamination levels enclosed within a tank.

In addition, the disclosed cold plasma Device has many uses in different fields and applications, such as, inter alia, control of air flow over a variety of airfoil surfaces, including missiles, airplane wings, airplane rudders and the like. Use of the Devise for plasma actuation may provide rapid control of the air flow for enhanced control of the direction and maneuverability. Such uses include those disclosed in U.S. Pat. Nos. 7,070,144, and 7,275,013; and U.S. Patent Applications 2006/0005545, and 2007/0089795, each of which is incorporated herein in its entirety. For example, US Patent Application 2007/0089795 discloses a fluid actuator, or a plurality of actuators, having two conductors, or a plurality of conductors, on a dielectric. The application of voltage to a conductor may form a plasma flow which can be modified and controlled in a desired direction.

Also disclosed are microwave absorbing characteristics of discharge plasmas which may form a "plasma shield" at higher intensities. Such a plasma shield would prove an effective defense against beamed-microwave directed energy weapons. Moreover, where a plasma absorbed such directed energy, the plasma's degree of ionization will increase, to become more effective and self-reinforcing. Such disclosures include U.S. Pat. Nos. 4,897,285 and 6,492,951, which are incorporated herein in their entirety.

The Device, and its bulk resistor system, may be employed with any of the incorporated disclosures, above. The Device may provide highly efficient applications of plasma having greater plasma output over a greater surface area, according to the desired use.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

The invention claimed is:

1. A decontamination device comprising:
    a gas manifold having an input coupled to a gas source, the gas manifold having a first surface and a second surface opposite the first surface, the first surface configured to be placed adjacent to a surface of an external object;
    a first plurality of output channels operatively formed on the first surface of the gas manifold, each output channel having an individual wire electrode with a sharp conductive point disposed therein; and
    a resistor network disposed adjacent to the second surface outside of the gas manifold and coupled to each of the individual wire electrodes, the resistor network further coupled to a power source for supplying the same electrical potential to each of the individual wire electrodes, wherein each individual wire electrode is mounted on individual channels formed in the resistor network such that each individual wire electrode extends from the resistor network into the first plurality of output channels;
    wherein when each of the individual wire electrodes are powered by the power source with the same electrical potential and gas is flowing through the plurality of output channels as supplied via the gas manifold, each sharp conductive point of the individual wire electrode creates an electric field gradient which pull electrons off of molecules of the gas and ionizes the electrons to form a cold plasma beam at each of the plurality of output channels under atmospheric pressure so as to decontaminate or sterilize the surface of the external object in contact with the cold plasma beams.

2. A decontamination device of claim 1, wherein the gas is inert.

3. A decontamination device of claim 2, wherein the inert gas is argon.

4. A decontamination device of claim 2, wherein the inert gas is helium.

5. A decontamination device of claim 1, wherein the gas source is operatively connected to the gas manifold via a conduit.

6. A decontamination device of claim 1, wherein at least one individual resistor forms the resistor network.

7. A decontamination device of claim 1, wherein a plurality of individual resistors form the resistor network, an individual resistor being coupled to a corresponding individual wire electrode.

8. A decontamination device of claim 1, wherein the gas manifold is configured as a hand-held applicator.

9. A decontamination device of claim 8, wherein the hand-held applicator is flexible to adjust to contoured surfaces.

10. A decontamination device comprising:
a gas manifold having an input coupled to a gas source, the gas manifold having a first surface and a second surface opposite the first surface;
a plurality of output channels operatively formed on the first surface of the gas manifold;
a plurality of wire electrodes, each wire electrode having a sharp conductive point, wherein an individual wire electrode of the plurality of wire electrodes is disposed in each output channel;
at least one resistor network disposed adjacent to the second surface outside of the gas manifold and coupled to the plurality of wire electrodes, the at least one resistor network further coupled to a power source for supplying the same electrical potential to each of the plurality of wire electrodes, wherein the at least one resistor network is at least one bulk distributed resistor, the at least one bulk distributed resistor being formed of an insulating material that blended with at least one conductive component to produce a desired level of equivalent resistance throughout the at least one bulk distributed resistor,
wherein when the plurality of wire electrodes are powered with the same electrical potential and gas is flowing through the plurality of output channels, each sharp conductive point creates an electric field gradient which pull electrons off of molecules of the gas and ionizes the electrons to form a plasma beam at each of the plurality of output channels under atmospheric pressure.

11. A decontamination device of claim 10, wherein the at least one bulk distributed resistor is formed with a pin array.

12. A decontamination device of claim 10, wherein the at least one conductive component is selected from the group consisting essentially of carbon nanotubes, carbon fibers, graphite powers, conductive metal particles, conductive metal oxides, conductive polymers and combinations thereof.

13. A decontamination device of claim 10, wherein the power source directs power through the at least one bulk distributed resistor.

14. A decontamination device of claim 13, wherein the power flows through the at least one bulk distributed resistor and operatively connects with the gas manifold to flow into the gas manifold and ionize the gas.

15. A decontamination device of claim 14, wherein the ionized gas forms a plasma beam.

16. A decontamination device of claim 15, wherein the plasma beam flows through an emitter.

17. A decontamination device of claim 16, wherein the emitter carries the plasma beam through an applicator.

18. A decontamination device of claim 17, wherein the applicator is located above a surface to be decontaminated or sterilized.

19. A decontamination device of claim 18, wherein plasma beam contacts the surface.

20. A decontamination device of claim 19, wherein the surface is decontaminated or sterilized.

* * * * *